US009886828B1

United States Patent
Tavares (10) Patent No.: US 9,886,828 B1
(45) Date of Patent: Feb. 6, 2018

(54) RESPONDING TO AN ALERT MESSAGE RECEIVED FROM AN EVENT NOTIFICAITON SYSTEM

(71) Applicant: David Tavares, Kleinburg (CA)

(72) Inventor: David Tavares, Kleinburg (CA)

(73) Assignee: Globestar Systems, Inc., Toronto (CA)

( * ) Notice: Subject to any disclaimer, the term of this patent is extended or adjusted under 35 U.S.C. 154(b) by 0 days.

(21) Appl. No.: 15/407,768

(22) Filed: Jan. 17, 2017

(51) Int. Cl.
H04W 24/00 (2009.01)
G08B 5/22 (2006.01)

(52) U.S. Cl.
CPC .................... G08B 5/223 (2013.01)

(58) Field of Classification Search
None
See application file for complete search history.

(56) References Cited

U.S. PATENT DOCUMENTS

| 8,825,043 | B2* | 9/2014 | Rogalski | H04M 1/2725 455/404.1 |
| 8,938,256 | B2* | 1/2015 | Logan | G08B 13/1427 340/988 |
| 8,996,630 | B2* | 3/2015 | Wilson | H04L 51/16 709/206 |
| 9,554,261 | B1* | 1/2017 | Tavares | H04W 4/22 |

* cited by examiner

Primary Examiner — K. Wong
(74) Attorney, Agent, or Firm — Robert Schuler (57) ABSTRACT

An alert message application running in associated with an alert message response system and is configured with softkeys, each one of which is associated with an alert message response option that is displayed by a mobile communication device depending upon a type of alert message received by the mobile communication device from an event notification system. A mobile communication device user can select one of the displayed response options which causes coded information (response code) representing the selected response option to be included in an alert response message sent to the event notification system (ENS). The ENS uses the response code to determine whether to take an action.

20 Claims, 10 Drawing Sheets

RESPONDING TO AN ALERT MESSAGE RECEIVED FROM AN EVENT NOTIFICAITON SYSTEM

1. FIELD OF THE INVENTION

The present disclosure relates to an event notification system (ENS) and mobile communication devices that receive and respond to alert messages from the ENS.

2. BACKGROUND

An event notification system (ENS) can operate in many different types of environments to receive messages, from a variety of input devices and systems, that have information about many different types of events, they can operate to determine how to react to information received in the messages and to generate and send an alert message to one or more individuals, and they can operate to receive and process responses to the alert messages. An ENS can be configured to operate in a number of different environments, such as a financial environment, emergency service environment, manufacturing environment, in healthcare environment and in many other types of environments. When operating in a healthcare environment, an ENS can receive information in an event message generated by a number of different types of event sources or call points, such as a patient monitor, a nurse call station, or any other type of call point employed in a healthcare setting. The ENS can operate to determine the origin/source of an event message, and it can determine whether or not to take further action with respect to the information comprising the event message. As a result of receiving an event message, the ENS can determine that an alert message should be generated and sent to one or more clinicians, and then wait for an alert response message that has response information the ENS can use to determine whether to take any further action, such as escalating the event to another clinician.

Figure 1A:
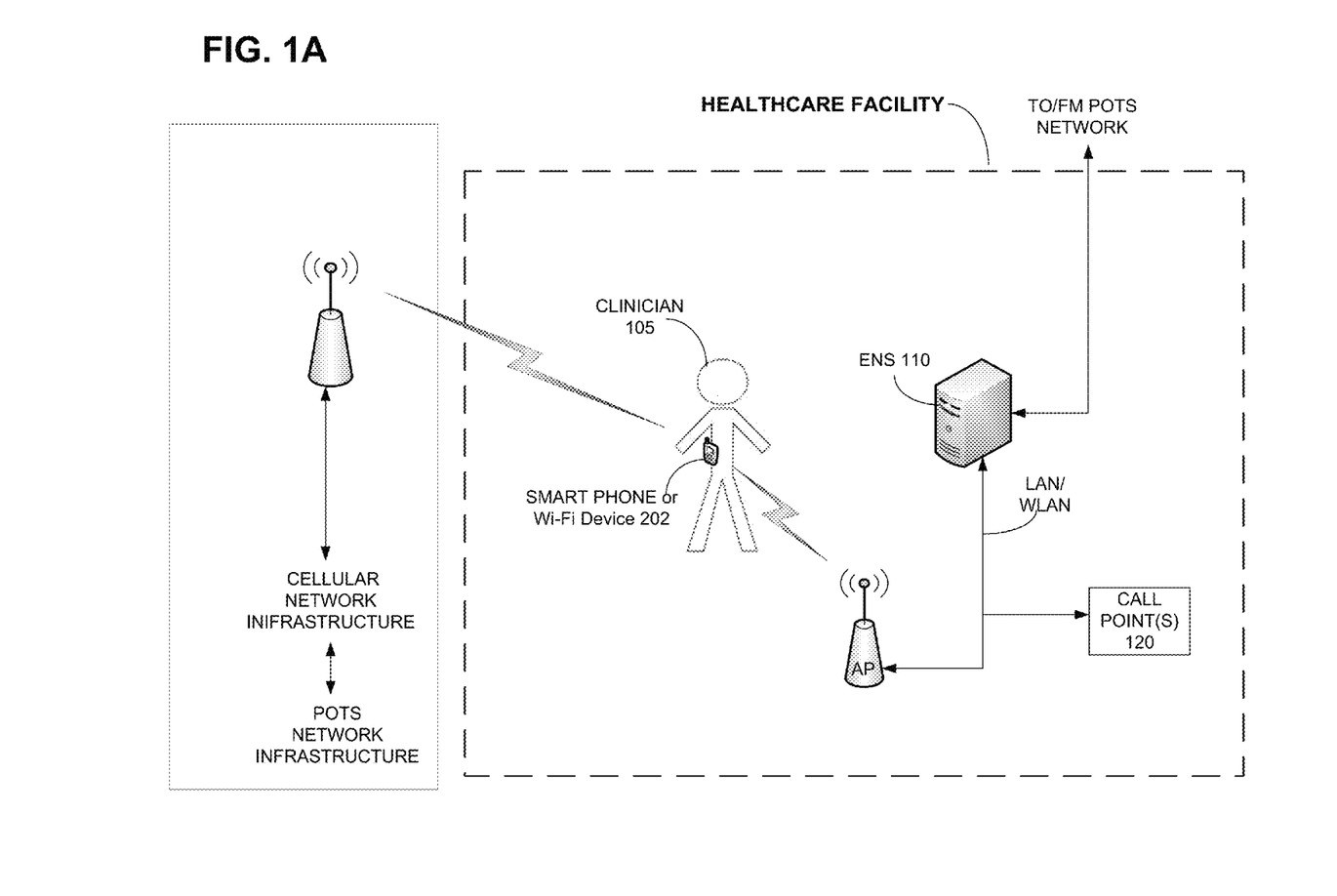
FIG. 1A is a diagram illustrating a wireless communication network in a healthcare facility connected to an event notification system.

Event notification systems can be configured to link with wireless networks and to send alert messages to and receive alert response messages from mobile communication devices (i.e., wireless communication badge, smart phone or Wi-Fi phones). When configured to communicate over a wireless network, it is not necessary for medical staff to be paged, and then have to locate the closest wired communication device (i.e., POTS phone) in order to respond to an alert message. Instead, staff can use their mobile device to immediately respond to an alert message regardless of their location, and provided their mobile communication device is within range of a wireless network. This wireless notification and response capability has improved medical staff response times to patient emergencies, and generally improved the efficiency and patient satisfaction with which staff is able to work in a healthcare environment. FIG. 1A shows an event notification system (ENS), located in a healthcare facility, that is configured to connect with two types of wireless networks (Cellular & Wi-Fi), and a wired (POTS) communication network. The ENS operates to send alert messages over either the Wi-Fi or Cellular network to a mobile communication device associated with a healthcare staff member (clinician), and it operates to receive alert message responses generated by the clinician from the mobile device. The ENS is also connected to a plurality of event generation devices such as patient monitors and to other types of call points. The patient monitors and other types of call points respectively operate to detect physiological information relating to a patient and to detect requests or other information entered by a clinician and to send this information to the ENS. The call points are positioned strategically throughout the healthcare facility to serve as an ENS communication portal for the staff.

3. BRIEF DESCRIPTION OF THE DRAWINGS

The present invention can be best understood by reading the specification with reference to the following figures, in which.

4. DETAILED DESCRIPTION

While event notification systems can be configured to send alert messages (voice or text alert messages) to and receive alert response messages from mobile devices, some mobile devices require that a user handle the device in order to respond to an alert message, or if the mobile device can recognize verbal commands, audio information in a verbal response needs to be converted to textual information at the mobile device or at an ENS before the ENS can use the information to determine if any action should be taken, such as escalating the response by sending the same alert to another staff member. Further, textual information in an alert response message received by the ENS has to be analyzed before the ENS is able to determine if it should initiate any further action. In this regard, the ENS can employ key word matching methods to determine the meaning of a response. So for instance, if an alert message prompts a mobile device user to respond by acknowledging the alert, the user can utter a response (i.e., ACKNOWLEDGE/YES/NO), then functionality in either the mobile device or the ENS can convert the verbal response information to text response information, and functionality in the ENS can operate on the text information in the response to determine what the text information means. After the ENS understands the meaning of the response, it can then determine whether it should initiate an action or not. While the ability to respond to an ENS alert message verbally is very convenient for healthcare staff, it requires that additional functionality (speech to text conversion and text recognition) be implemented in a mobile communication device and/or in the ENS. This additional functionality adds cost and complexity to the mobile device and ENS, and the response back from the mobile device may occupy a voice channel.

In order to lower the cost and complexity of a mobile communication device that is in wireless communication with an event notification system, I have designed the mobile communication device to enable a set of softkey based alert message response options that corresponds to a type of alert message received by the mobile communication device, and each softkey response option in the set is associated with a particular alert message response, which is in turn associated with a particular response code. Subsequent to a user selecting an alert message response option, the mobile communication device can generate an alert response message which has a response code, associate with the option selected, that the ENS can use to determine an action to take. Each softkey response option that is enabled represents an appropriate response that the device user can select, such as "Acknowledge", "Callback" or "Escalate".

The softkey alert message response options can be implemented in virtual sofkeys or in physical softkeys, and according to one embodiment, a simple communication FOB, operating with short range wireless technology, can be configured to operate all of the softkey alert message response option functionality, and in another embodiment, a cellular or WIFI communication device can be configured to operate all of the softkey alert message response option functionality, and in another embodiment, a portion of the softkey alert message response functionality can be implemented on the communication FOB and the remaining portion of the softkey alert message response functionality can be implemented on the cellular or WIFI device. Regardless of the embodiment, the softkey alert message response functionality can be implemented in firmware or software as a mobile alert message application that can operate to receive an alert message and determine what type of alert message is received, and depending on the alert message type, it can operate to enable one or more physical softkeys or virtual softkeys on the mobile communication device. As described earlier, each physical or virtual softkey instance is associated with a unique alert response code that represents a particular response to an alert message received by the mobile communication device from the ENS. The mobile communication device user has only to select a physical or virtual softkey in order to control the device to generate a response to the alert message, and this alert response message can be comprised of only the unique code that the ENS can use to determine whether an action (i.e. send another alert message to the same or different clinician) should be taken. While the information in the payload of the alert response message generated as a consequence of selecting a softkey is described as only comprising an unique alert response code, this response message can have other information, but the alert response code is the only information the ENS needs in order to determine whether to take other action (i.e. escalate the alert, terminate the alert, etc.).

FIG. 1A illustrates the embodiment in which all of the functionality comprising the entire mobile alert message application is running on a cellular or WIFI enabled communication device (mobile communication device or simply mobile device 2020). The mobile device can be in communication with an ENS 110 over a cellular or WIFI link, and the ENS can be in communication with some number of call points over a LAN or WLAN.

Figure 1B:
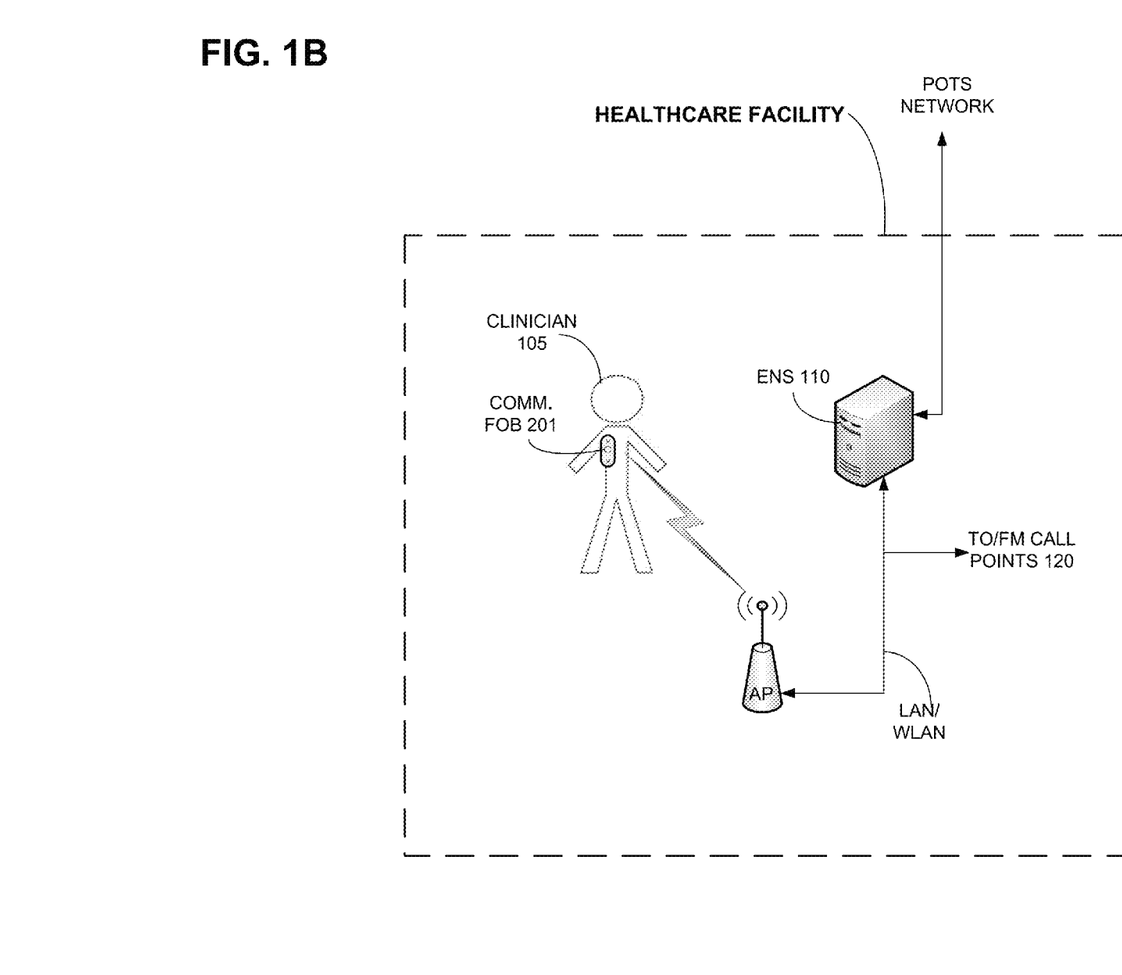
FIG. 1B is a diagram of a communication network that is similar to that in FIG. 1A with a communication FOB 201 replacing the smart phone 202.

FIG. 1B illustrates an embodiment in which all of the functionality comprising the mobile alert message application is running on a communication FOB 201 that is associated with and operated by a clinician 105. In this case, the FOB 201 is configured with WIFI or DECT or some other medium range communication technology, and is in communication with the ENS 110 over the combination of a wireless and wired link which can be in communication with some number of call points over the LAN or WLAN.

Figure 1C:
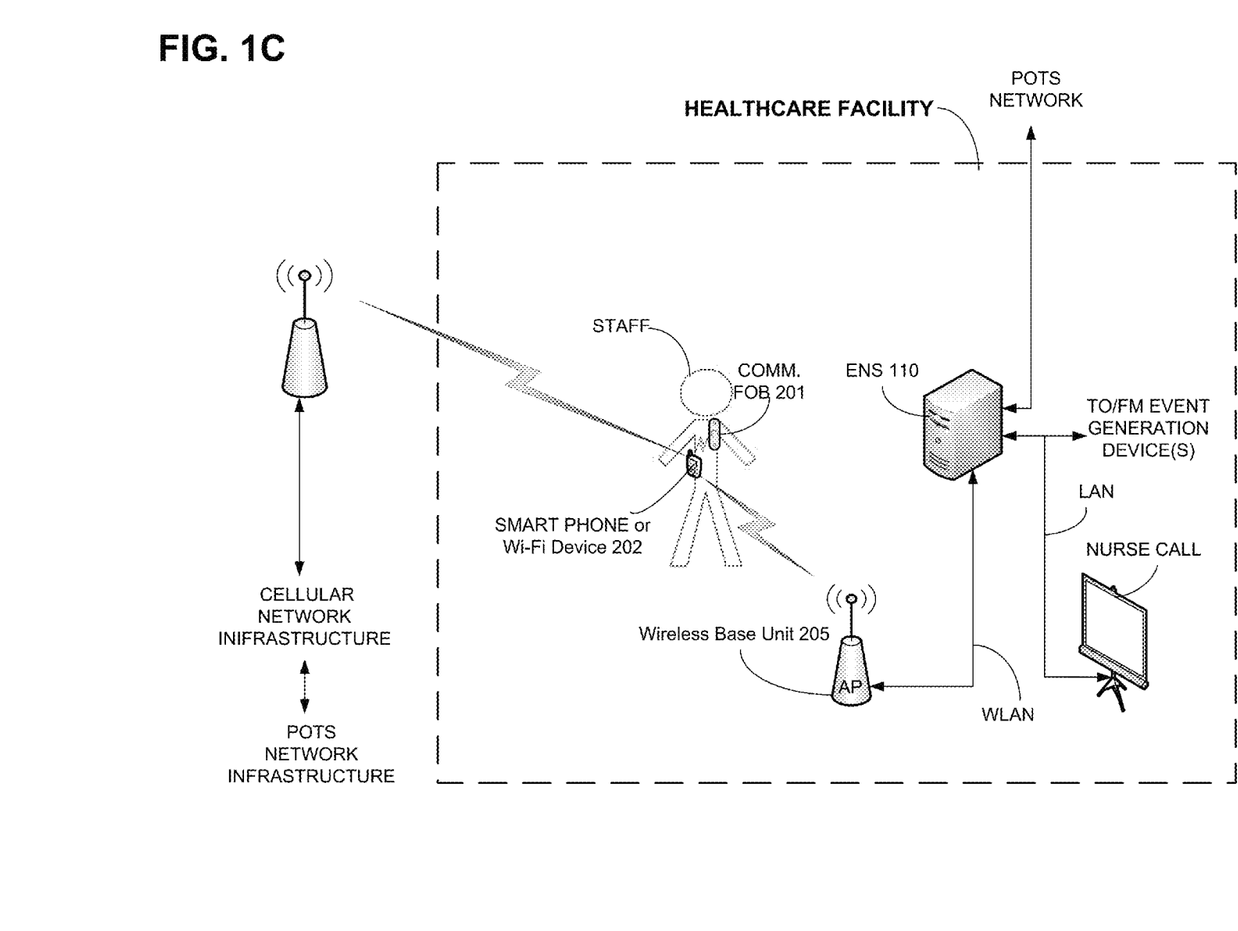
FIG. 1C is a diagram of a communication network that is similar to that FIG. 1B with the addition of a communication device 202 in communication with the FOB 201 of FIG. 1B over a short range wireless link.

FIG. 1C illustrates an embodiment in which a portion of the mobile alert message application functionality is running on a cellular, WIFI or DECT enabled device (mobile device 202) that is in short range communication with a communication FOB 201 that is running another portion of the mobile alert message application functionality. According to this embodiment, the portion of the mobile alert message application running on the mobile device operates to receive an alert message from the ENS 110, identifies a type of the alert message, and sends softkey enable instructions corresponding to the alert message type in a short range wireless Bluetooth message to the FOB 201. The FOB 201 can have a display or not, and the portion of the mobile alert message application running on the FOB can use the softkey enable instructions in the Bluetooth message to alert the FOB user (either display a message or play an alert or both) to select an appropriate one of the enabled softkeys.

Figure 2:
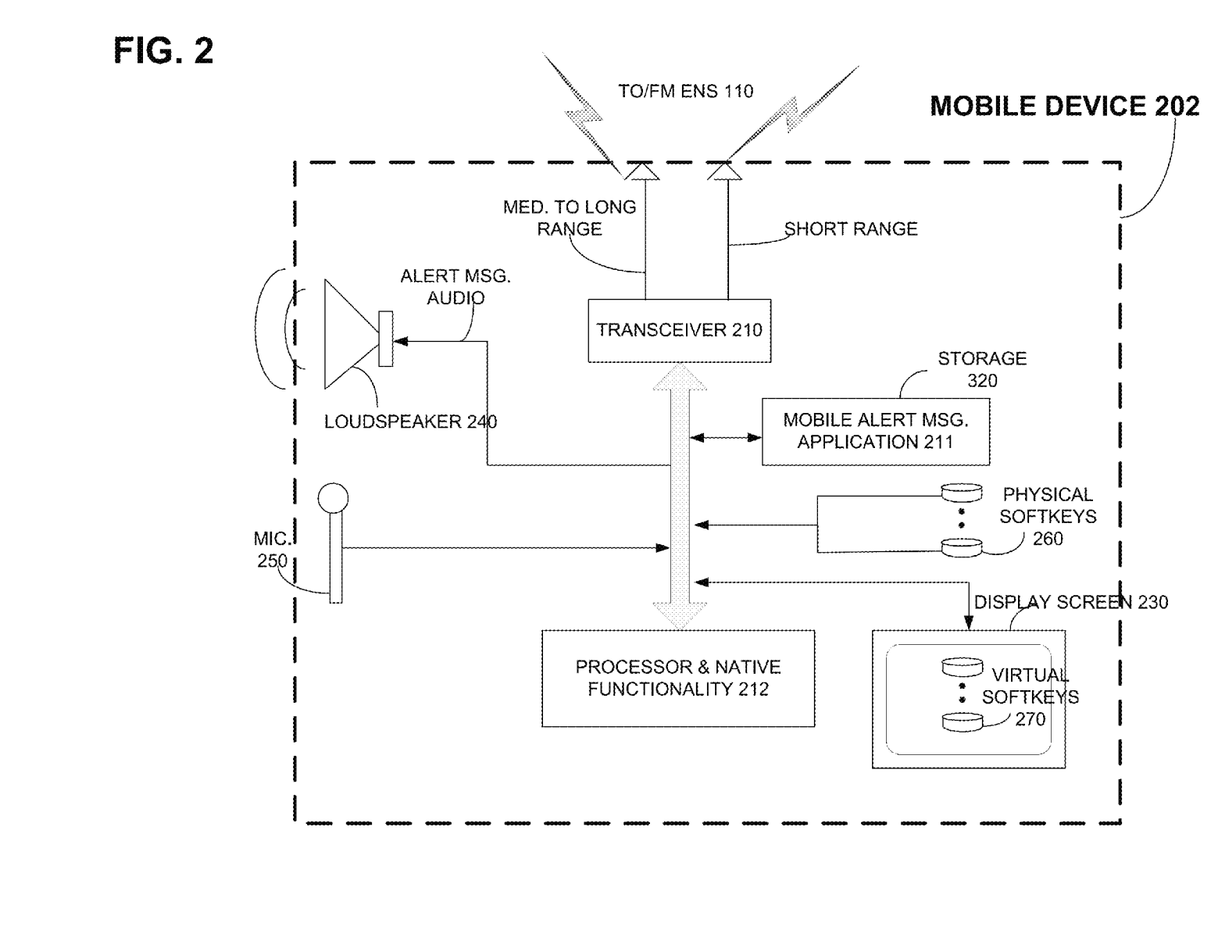
FIG. 2 is a block diagram illustrating.

Different elements comprising the overall functionality of the mobile alert message application can be implemented on a number of different devices. For example, some of the application functionality can be implemented on the ENS 110, some on the mobile device 202 and the remaining functionality can be implemented on the FOB 201. In another embodiment, some of the application functionality can be implemented on the mobile device 202 and the remaining functionality can be implemented on the FOB 201. However, for the purposes of this description, the functionality comprising the mobile alert message application is considered to be implemented entirely in the mobile device 202, shown with reference to FIG. 1A. In this regard, the mobile device 202 in FIG. 2 is comprised of a transceiver 210 which can operate to establish a connection over a variety of wireless networks with the ENS 110, and to transmit and receive information to and from the ENS or some other communication device also connected to the network. The wireless network can have devices that are configured to support any long to medium range wireless communication technology such as cellular or WiFi/DECT technology, and it can have devices that are configured to support any short range wireless communication technology such as Bluetooth, for example, or these devices can be configured to support both long/medium range wireless communication and short range wireless communication. The mobile device 202 also has a processor 212 that controls the operation of various functions associated with the mobile device, such as a display 230, a loudspeaker 240, a microphone 250, and some number of physical buttons 260 that can be programmed with softkey functionality. The processor also controls the operation of a mobile alert message application 211 which is comprised of computer instructions that, among other things, cause the device 202 to operate on information received from the ENS 110 to notify a mobile device user to an incoming alert message, to identify a physical or virtual softkey corresponding to a type of the incoming alert message and to enable response options for selection by the mobile device user, to detect which softkey the user selects, and to place a unique alert response code that corresponds to the selected response option into an alert response message that is transmitted to the ENS 110.

The mobile device 202 generally operates to receive an alert message that has, among other things, information relating to a type of the alert message (either explicit or implicit information). The selection of a particular softkey set (physical or virtual) for which a corresponding one or more response options are enabled, depends upon the type of alert message generated by the ENS 110. The response options that can be enabled are comprised of, but are not limited to, Acknowledge, Callback, Escalate the Alarm, Complete the Request, Cancel the Request, Ignore, Contact Supervisor, Show More Alert Details, Delayed, Alarm Silenced, Patient Dropped Off, Patient Picked Up, Porter Requests Nurse Assist, Patient is Ready, Patient is Not Ready, On Short Break, Lunch Break, In Service, Patient Lab Results Received, Patient Lab Results Not Received, Patient On Route, Patient Request Assist, Reviewed the Document, Consulted, Rounding Compete, Fall Risk Profile Changed, and System Updated options.

As will be described later in more detail, the selection of a softkey set for which associated response options are enabled, depends upon the type of alert message received by the mobile device 202, and each of the softkeys that are enabled are associated with a unique response code, which response code can be numerical code, alpha-numeric code or a code comprised of one or more letter of an alphabet. The mobile device 202 can alert the device user to the arrival of an alert message from the ENS with an audible sound, a light emitting element, or with a vibration, and the mobile device can present response options from which the user can select in the form of the virtual or physical softkeys. In the case that response options are enabled as virtual softkeys, information associated with each response option (i.e., ACK, Callback, Escalate) can be displayed in a separate field on the display 230. In this case, the mobile device can have a touch sensitive screen on which the response options can be displayed for users to select by merely touching a field or icon that represents a particular response option. In the case that the response options are presented in the form of physical softkeys, information associated with each option can be conveyed to the user in an audible message played on the loudspeaker by the mobile device (i.e., depress physical button 1 for ACK, depress physical button 2 for Callback and so forth). In either case, the selection by the mobile device user of at least one response options causes the mobile alert message application 211 to generate an alert response message that has a response code which corresponds to the response option selected by the mobile device user. A response code includes information that the ENS 110 can use to determine whether further action should be taken.

Figure 3:
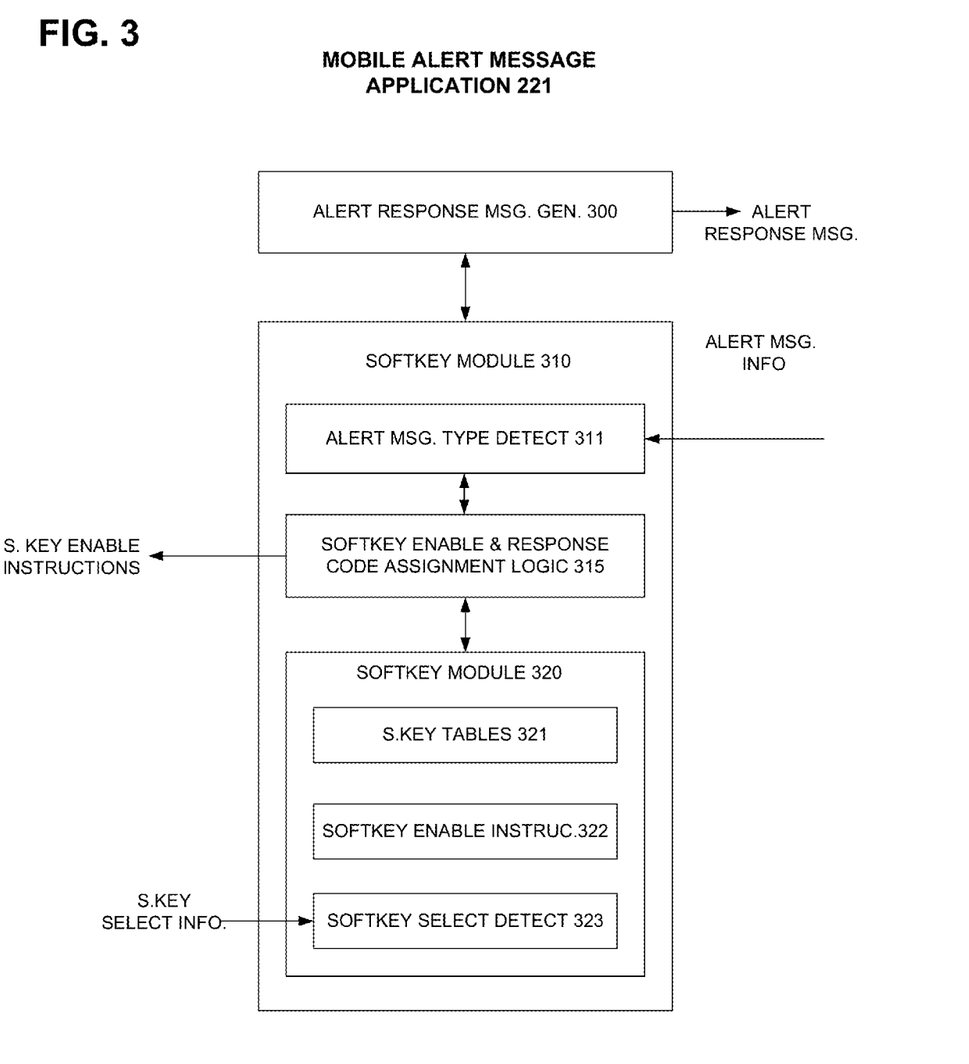
FIG. 3 is a block diagram illustrating.

The functional elements comprising the mobile alert message application 211 will now be described with reference to FIG. 3. The mobile alert message application 211 is comprised of an alert response message generator 300 and a softkey module 310. The alert response message generator 300 generally operates, under control of the processor 210, to format an alert response message with alert response information and to pass this information in a message to the transceiver 210 for transmission to the ENS 110. The alert response information can include, among other things, an alert response code, a unique identity of the mobile device 202, a time at which an alert response message is generated, and the current location of the mobile device 202. The overall format of the alert response message is dependent upon the particular wireless communication protocol running on the mobile device 202, and so will not be described here in detail other than to mention that the alert response information can be included in a payload portion of the alert response message and be formatted in a manner that the ENS 110 is able to use. The softkey module 310 is comprised of a number of functional elements that generally operate to identify an alert message type, select a particular softkey set that depends upon the identified alert message type, and to enable response options associated with a softkey instance comprising the softkey set, and to detect which response option a mobile device user selects. An alert message type detector 311 generally operates to receive alert messages from the ENS 110, and to parse the alert message looking for key implicit information that can be used to determine the purpose of the message or looking for key explicit information relating to the alert message type. Key implicit information can include, but is not limited to, the source of an alarm (i.e., patient monitor, ER, nurse station, or some other type of call point), and other information in the message that is an indicator of the message purpose, and key explicit information can include an unambiguous identity of an alert message type that is placed into an alert message by the ENS 110. So with respect to key implicit information, if an alarm is generated by a particular patient monitor, then the purpose of the alert message can be to instruct a caregiver to attend to the patient in a particular bed associated with that monitor, if the alarm is generated by an ER doctor, then the purpose of the alert message can be to request that the caregiver assist the doctor in the ER. So in addition to the source of an alarm (unique monitor identity), the alert message generated by the ENS 110 can include the time that the alert is generated, the name of the patient in the bed, the alert criticality level. Optionally, the ENS 110 can include a code in the alert message that the detector 311 can use to determine what type of alert message is received.

Figure 4A:
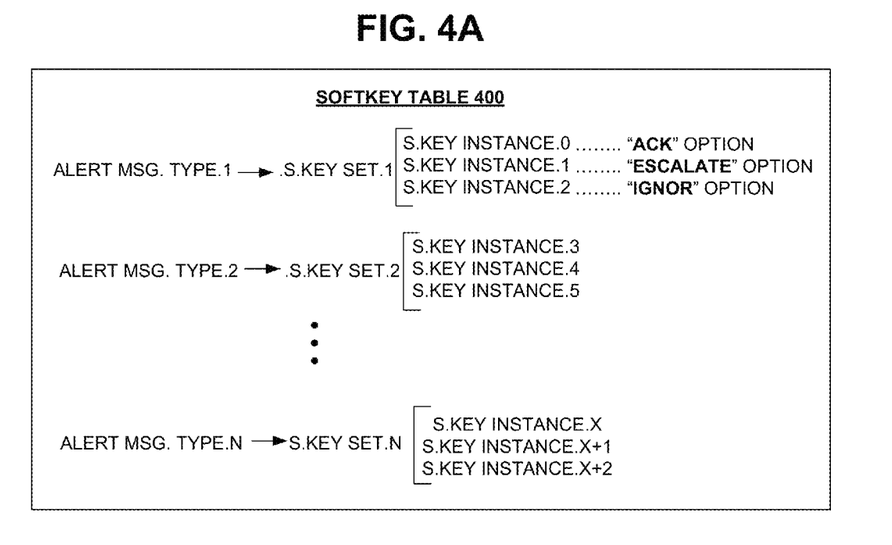
FIG. 4A is a diagram showing a softkey table 400.
Figure 4B:
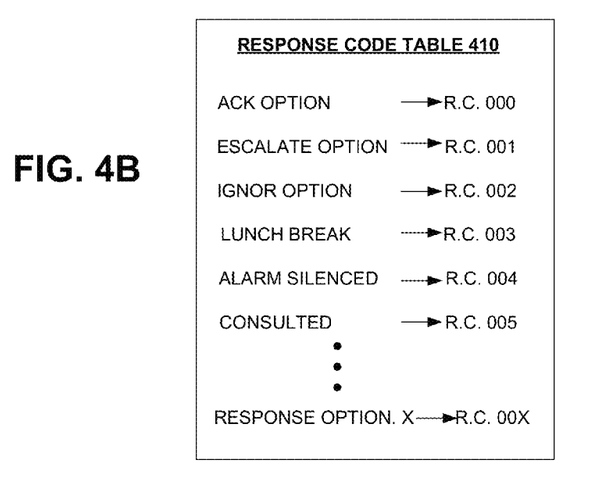
FIG. 4B is a diagram showing a response code table 410.

Subsequent to the mobile device receiving an alert message and determining the alert message type, the logic 315 can use the alert message type information to identify which one of a plurality of sets of softkeys to select. In this regard, FIG. 4A shows a table 400 that relates each of a plurality of alert message types to a particular set of softkeys, corresponding softkey instances and response options. The table 400 shows each softkey set as being comprised of three softkey instances, but any set can have more or fewer softkey instances. The logic 315 can use the alert message type information as a pointer into the table 400 to identity a softkey set, and to identify the softkey instances corresponding to the set, and to identify response options that can be displayed on the mobile device for selection by the mobile device user. Each response option represents instructions that cause it to be displayed (in the event that a virtual softkey is selected) on the mobile device screen for selection by the user. Several of the response options shown in the Table 400 are also shown in table 410 with reference to FIG. 4B. This table shows an association between each response option and a unique response code (R.C.) which can be included in an alert response message sent to the ENS 110. This response code can be a numeric code such as 001, 002, 003, an alpha-numeric code such as A1B or 12C, or it can be comprised of an unintelligible sequence of letters such as "AVFR". Including a response code in a response message sent to the ENS 110, as opposed to including voice information or a string of textual information, greatly simplifies the functionality implemented in the alert message application 321 and in the ENS 110 needed to process an alert response message.

Figure 5A:
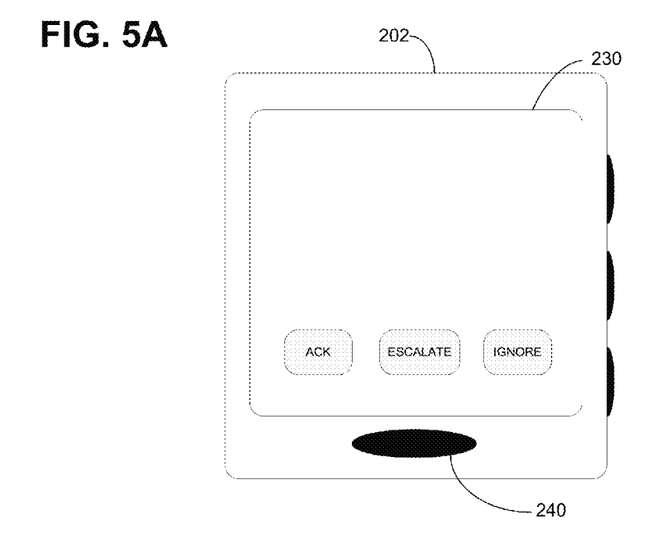
FIG. 5A is a block diagram showing functional elements in a training module 235 comprising the mobile communications device 200.
Figure 5B:
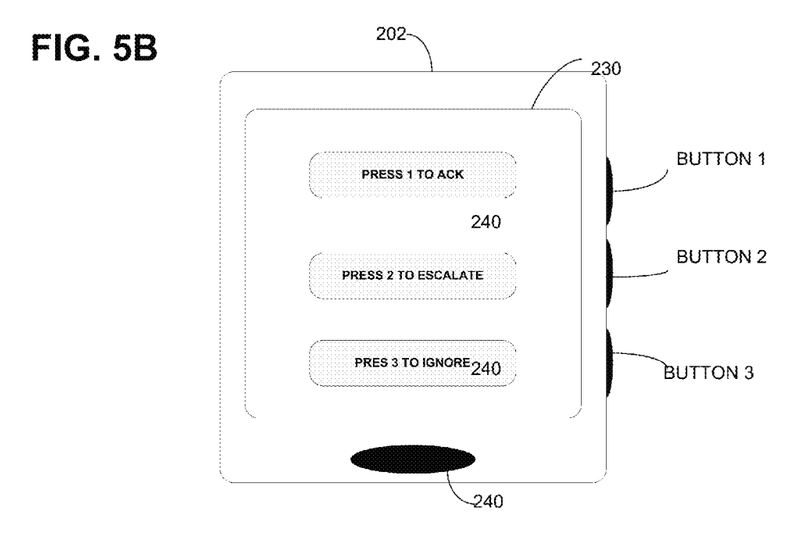
FIG. 5B is a diagram illustrating functional elements comprising a wireless communication device 201 having only short range wireless communication capability.
Figure 5C:
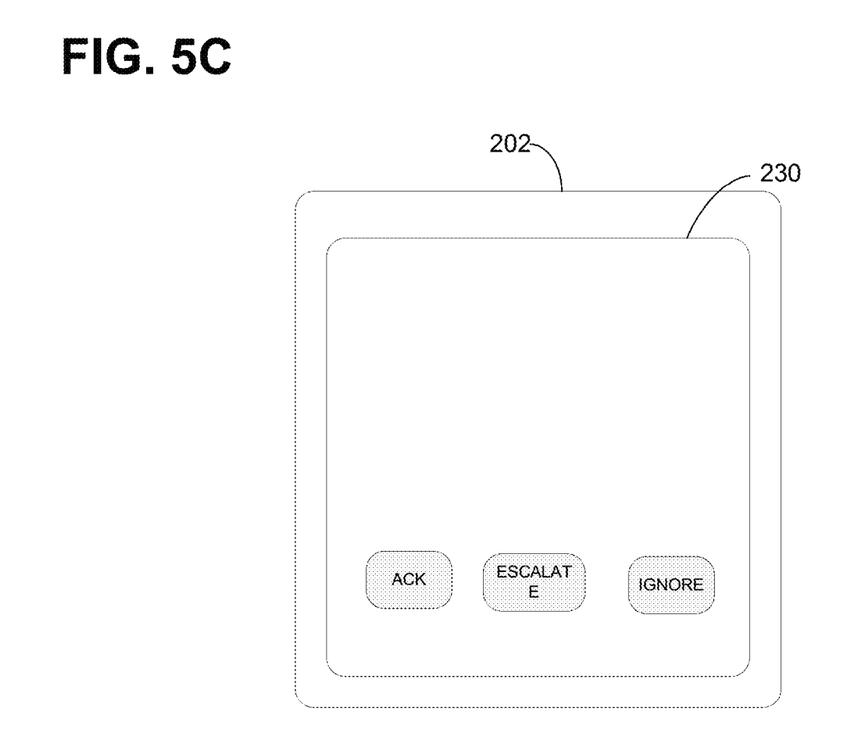
FIG. 5C is a diagram illustrating functional elements comprising an alert message application 500 running on the wireless communication device 202.

As described above and with continued reference to FIG. 3, the instructions found in the instruction table 322 are used by the processor 212 to cause one or more response options to be enabled/displayed by the mobile device 202 on the screen 230 for selection by the device user as illustrated in FIG. 5A. In addition to information used to identify an alert message type, an alert message can include annunciation information that in some manner notifies the mobile device user that they should respond to an alert message by selecting one of the options displayed on the screen. The device user has only to examine the touch screen 230 and select a response option in order to generate and send an appropriate alert response message having a corresponding response code. Alternatively, if the mobile device is configured with physical softkeys, the mobile device can play or display instructions that the user can follow to select a response option.

The functional elements and general operation of the ENS 110 will now be described with reference to FIG. 6. The ENS 110 generally operates to receive event messages from event generation devices (i.e., call points or some other device or process that triggers an event) and/or other systems connected to the healthcare network in FIG. 1C, to generate and send alert message to one or more mobile devises under control of appropriate individuals, and to receive and process responses to the alert messages from each mobile device. The ENS 110 has an Event Message Processor 610, and Alert Message Generation module 620 and a Response Message Processor 630. The Event Message Processor 610 operates to receive event message information from event message generation devices and parses the event message information looking for information relating to the source of an event message (particular geographic location such as a room number), and looking for information relating to a type of event An event message is formatted such that the position of the event location information, event type information, and additional relevant event information in the event message is known by the ENS 110. This allows the ENS to parse each event message and identify information relating to location information and event type information. Information relating to an event location can be a unit and a room number. where the unit can be an emergency room (ER) unit, a cardiac (CA) unit or any other type of unit located in a healthcare setting, and the room number information can include a number and a letter, such as 412A. Alternatively, the event location information can be more general, such as a zone or area designation like, zone-1 or west corridor. The event type information can include such things as heart rate (HR) information, respiratory rate (RR) information, blood pressure (BP) information, or any other monitored patient physiological alarm information.

After the event source location information and the event type information are detected, the processor 610 can perform a key character (alphanumeric) type matching operation during which the detected alphanumeric location and event type information are compared to alphanumeric characters in a plurality of standard alert message stored in association with the processor 610. The ENS 110 is able to identify which one of a plurality of event messages to send when there is a match between the information in the event message and information in a standard alert message, and the processor can send the identity of the alert message and the event location and type information to the Alert Message Generation module 620.

The module 620 uses information in a staff roster (identity of an individual or individuals currently on duty and who are responsible for particular types of events in particular locations, the network address of a FOB assigned to this/these individuals areas) to identify one or more individuals who should receive the alert message. The generator 620 then formats an alert message with the event location and event type information, sends the alert message to the appropriate staff, and sends a message to the Response Message Processor 630 that has information indicating what type of event message was sent, indicating what valid response options/codes to expect, and indicating to which individual (s) the event message is sent and when.

Figure 6:
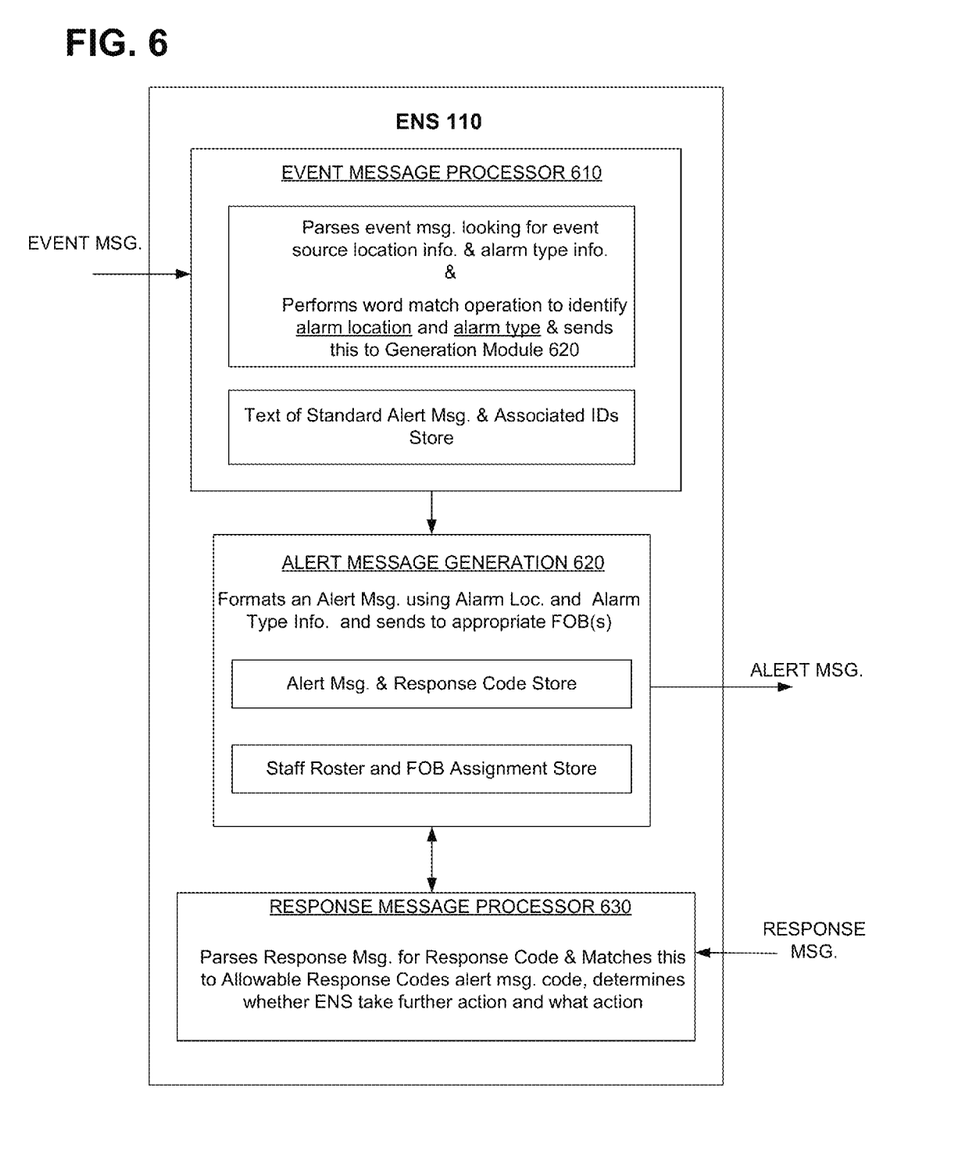
FIG. 6 is a high level block diagram illustrating functional elements comprising an event notification system (ENS) 110.

With continued reference to FIG. 6, the Response Message Processor 630 can receive an alert response message having a response code from one of more mobile devices 202. It examines the response message for the response code, and if it detects a valid response code, it uses this code to determine whether to cancel the alert, escalate the alert, to send another alert to the same FOBs, or to take any other action.

The operation of the logic 315 to control the softkey module 310 comprising the mobile alert message response application 211 will now be described with reference to FIG. 7. According to the embodiment described below with respect to FIG. 7, the mobile alert message application 211 is configured to enable virtual softkey functionality, but it should be understood that the other configurations are possible. The application 211 can also be configured to enable physical softkey functionality, or it can be configured to enable both virtual and physical softkey functionality on the same mobile device. The particular configuration that is desirable can depend upon the capabilities of the mobile device or the combination of mobile devices in which the application 211 is implemented.

Figure 7:
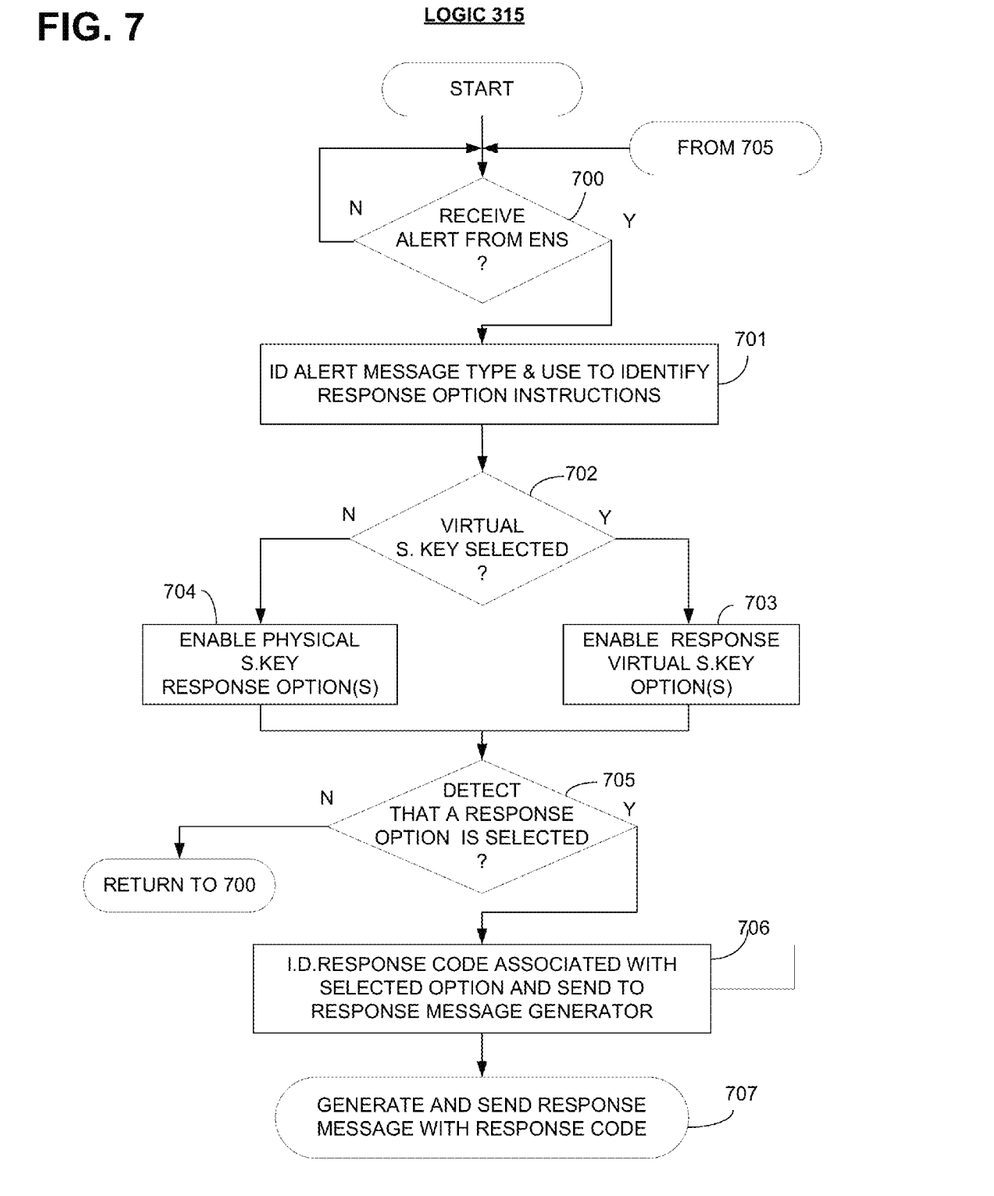
FIG. 7 is a logic diagram showing the operation of softkey control logic 315.

Referring now to FIG. 7, subsequent to the ENS 110 receiving an event message from a call point, the ENS can generate an alert message for transmission to a caregiver's mobile device that has information (either implicit or explicit) that can be examined to determine an alert message type. At 700, the logic 315 running on the mobile alert message application 211 is continually monitoring the operation of the alert message type detector 311 comprising the mobile alert message application looking for alert messages received from the ENS. After an alert message is received, at 701 the detector 311 parses the alert message contents and examines the parsed contents to identity the alert message type, and the identity of the alert message type is used as a pointer into the softkey table 400, described with reference to FIG. 4A. The table 400 is comprised of softkey information that is associated with each alert message type, and at 702 the logic determines that either a set of virtual of physical softkeys should be selected. Assuming the application 211 is configured with virtual softkeys, then the process proceeds to 703, and the logic can use response option display instructions stored in association with the table to display one or more alert message response options for selection by a mobile device user. At 705, the logic can detect that a displayed response option is selected, or not, and if so the process can proceed to 706, where the identity of the selected response (can be a binary code) option can be used as a pointer into the table 410, described earlier with reference to FIG. 4B, to identify an associated response code. So for example, if at 701 the logic determines that the alert message is a TYPE.1 message, then the softkey instances, S.KEY INSTANCE.0-S.KEY INSTANCE.2, comprising the softkey set, S.KEY SET.1, would be enabled, and the response options associated with each softkey instance (i.e., ACK, ESCALATE, and IRNOR) in the set would be displayed. Then, if the logic detected that the response option ESCALATE is selected, it can use the identity of the selected option (i.e., ESCALATE=binary code 1) as a pointer into the table 410 to lookup the corresponding response code, which in this case is the response code, R.C. 001. This response code is then passed to the alert response message generator 300 comprising the alert message application 211 where it is attached to the body of a response message and sent to the ENS 110.

According to the embodiment described above with reference to FIG. 7, and in contrast to prior art methodologies, there is no need for the user of the mobile device 202 to train the mobile device to recognize a response, whether the response is verbal or textual, and there is no need to configure the mobile device to have functionality to convert voice response information or textual response information into a data format that is compatible with the wireless transmission technology messaging format implemented on the mobile device, as the response code is already in the proper data format. Using such a softkey alert message response methodology simplifies the functionality needed by the mobile device 202 to process alert messages and alert message responses.

Subsequent to receiving the alert response message from the mobile device 202, the ENS 110 has only to examine the response code, and use this code to determine what action, if any, to take. More specifically, an alert response message is received by the response message processor 630 comprising the ENS 110, where it is parsed and the response code is identified and it is determined that the identified response code is an allowable code. Depending upon the information comprising the response code, the ENS can take no further action (ACK response code is received), send another alert message to another, different individual (ESCALATE respond code is received), or the ENS can simply receive an alert response message and take no action (IGNORE response code is received).

The forgoing description, for purposes of explanation, used specific nomenclature to provide a thorough understanding of the invention. However, it will be apparent to one skilled in the art that specific details are not required in order to practice the invention. Thus, the forgoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

I claim:

1. A method of formulating a response to an alert message generated by an event notification system, comprising:
   receiving an alert message at a mobile communication device and determining an alert message type by examining information in the alert message;
   using, by a mobile communication device in receipt of the alert message, the alert message type to select one or more of a softkey instance, each softkey instance being associated with one or more computer instructions that the mobile communication device uses to enable one or more corresponding alert message response options for selection by a mobile communication device user; and
   detecting that a response option is selected, and generating and sending to the event notification system an alert response message having a response code that uniquely corresponds to the selected response option.

2. The method of claim 1, further comprising the event notification system receiving the alert response message and using the response code to determine what action to take.

3. The method of claim 2, wherein the event notification system maintains a listing of acceptable response codes for each alert message type corresponding to the alert message that is transmitted to the mobile communication device.

4. The method of claim 3, wherein the event notification system compares the response code in the response message sent to it with all acceptable response codes associated with the alert message type prior to determining what action to take.

5. The method of claim 1, wherein the softkey instance can be virtual softkey functionality or physical softkey functionality.

6. The method of claim 5, wherein the response options associated with the virtual softkey functionality are displayed on a touch screen comprising the mobile communication device, and instructions for selecting the response options associated with the physical softkey functionality are displayed or played by the mobile communication device.

7. The method of claim 6, wherein the response code uniquely corresponding to the selected response option is a numerical code, an alpha-numerical code, or a code comprised of one or more alphabetical letters.

8. The method of claim 1, wherein the alert message type is determined by the examination of information comprising the alert message that explicitly or implicitly identifies the alert message type.

9. The method of claim 8, wherein implicit information identifying the alert message type is comprised of an event message source, and explicit information identifying the alert message type is comprised of the unambiguous identity of the alert message type.

10. An alert message response system, comprising:
    an event notification system in communication over a wireless network with a mobile communication device, the alert message response system running a computer application that receives an alert message and detects a type of the alert message and uses the alert message type to select one or more softkey instances and associated one or more computer instructions each one of which is used to enable particular response options for selection by a user of the mobile communication device, the computer application detecting that at least one response option is selected and generating and sending to the event notification system an alert response message having a response code that uniquely corresponds to the selected response option.

11. The system of claim 10, further comprising the event notification system receiving the alert response message and using the response code to determine what action to take.

12. The system of claim 11, wherein the event notification system maintains a listing of acceptable response codes for each alert message type corresponding to the alert message that is transmitted to the mobile communication device.

13. The system of claim 10, wherein the softkey instance can be virtual softkey functionality or physical softkey functionality.

14. The system of claim 13, wherein the response options associated with the virtual softkey functionality are displayed on a touch screen comprising the mobile communication device, and instructions for selecting the response options associated with the physical softkey functionality are displayed or played by the mobile communication device.

15. The system of claim 10, wherein the response code uniquely corresponding to the selected response option is a numerical code, an alpha-numerical code, or a code comprised of one or more alphabetical letters.

16. An alert message response system, comprising:
   a computer application running on a first wireless communication device that operates to receive an alert message and to detect a type of the alert message received from an event notification system, and using the detected alert message type to select one or more softkey instances each one of which is associated with computer instructions for enabling a particular one of a plurality of response options;
   sending the response option enabling instructions associated with each of the one or more response options in a message over a short-range communication link to a second wireless communication device that operates to enable the options for selection by a user of the second wireless communication device; and
   the first wireless communication device detecting that at least one of the response options enabled on the second communication device is selected, and generating and sending an alert response message to the event notification system having a response code that uniquely corresponds to the selected response option.

17. The system of claim 16, further comprising the event notification system receiving the alert response message and using the response code to determine what action to take.

18. The system of claim 16, wherein the softkey instance can be virtual softkey functionality or physical softkey functionality.

19. The system of claim 18, wherein the response options associated with the virtual softkey functionality are displayed on a touch screen comprising the mobile communication device, and instructions for selecting the response options associated with the physical softkey functionality are displayed or played by the mobile communication device.

20. The system of claim 16, wherein the response code uniquely corresponding to the selected response option is a numerical code, an alpha-numerical code, or a code comprised of one or more alphabetical letters.

\* \* \* \* \*